United States Patent
Käs et al.

(10) Patent No.: US 7,435,568 B2
(45) Date of Patent: Oct. 14, 2008

(54) OPTICAL CELL GUIDANCE METHOD AND APPARATUS

(75) Inventors: Josef Käs, Leipzig (DE); Mark Raizen, Austin, TX (US); Valery Milner, Basking Ridge, NJ (US); Timo Betz, Leipzig (DE); Allen Ehrlicher, Leipzig (DE)

(73) Assignee: Universitat Leipzig, Leipzig (DE)

( * ) Notice: Subject to any disclaimer, the term of this patent is extended or adjusted under 35 U.S.C. 154(b) by 220 days.

(21) Appl. No.: 10/293,142

(22) Filed: Nov. 13, 2002

(65) Prior Publication Data
US 2003/0109040 A1 Jun. 12, 2003

Related U.S. Application Data

(60) Provisional application No. 60/333,283, filed on Nov. 14, 2001.

(51) Int. Cl.
*C12N 13/00* (2006.01)
*G01B 11/02* (2006.01)
*G01B 11/04* (2006.01)

(52) U.S. Cl. .................... 435/173.1; 356/634
(58) Field of Classification Search ................ 435/368, 435/173.1; 356/634
See application file for complete search history.

(56) References Cited

U.S. PATENT DOCUMENTS

| | | | |
|---|---|---|---|
| 4,931,053 A | 6/1990 | L'Esperance | |
| 5,079,169 A | 1/1992 | Chu et al. | |
| 5,092,871 A | 3/1992 | Aebischer et al. | |
| 5,245,466 A | 9/1993 | Burns et al. | |
| 5,259,380 A | 11/1993 | Mendes et al. | |
| 5,464,436 A * | 11/1995 | Smith | 607/89 |
| 6,067,859 A | 5/2000 | Kas et al. | |
| 6,184,973 B1 | 2/2001 | Baer et al. | |
| 6,215,550 B1 * | 4/2001 | Baer et al. | 356/36 |

FOREIGN PATENT DOCUMENTS

WO PCT/US02/36456 11/2002

* cited by examiner

*Primary Examiner*—Jon P Weber
*Assistant Examiner*—Rosanne Kosson
(74) *Attorney, Agent, or Firm*—O'Keefe, Egan, Peterman & Enders, LLP

(57) ABSTRACT

Embodiments of the invention include Optical Cell Guidance (OCG) methods and apparatus to control cell growth. This system guides the leading edge of motile cells with an optical gradient, which biases the cell's motion into the light by pulling on proteins, which act like soft dielectrics in the electromagnetic field. OCG differs from those devices described above in that it controls the direction of cell motility. This is an entirely new field, and the first device to directly manipulate cell motility. OCG differs from current approaches in that it does not trap or hold particles. Instead of trapping and pulling the cell, the goal of OCG is to influence, direct, and control the growth of a growth cone.

10 Claims, 3 Drawing Sheets

Nerve growth biased to the left by laser (circled) with 100mW power. Growth cone outlined in dashes for clarity.

OPTICAL CELL GUIDANCE METHOD AND APPARATUS

CROSS-REFERENCE TO RELATED APPLICATION

This application claims the benefit of U.S. provisional patent application No. 60/333,283 entitled "Optical Cell Guidance Method and Apparatus," filed Nov. 14, 2001.

FIELD OF THE INVENTION

Embodiments of the invention are related to methods and apparatus for cell guidance. Certain embodiments are related to methods for guiding cells to produce a predetermined cellular structure, and/or a more elaborate cellular structure comprised of multiple cells, such as a network. In certain embodiments methods for the guidance of neurons are described.

BACKGROUND OF THE INVENTION

Current methods of directing the growth of cells are based on chemical gradients, polymer substrates, magnetic beads, or guidance channels. Methods involving polymer substrates and chemicals to direct neural growth are imprecise, static, and limited to two-dimensional applications. Magnetic bead steering is impractical due to the extensive preparation involved in attaching the beads to an axon, along with the added invasive risk. Electrically charged nerve guidance channels (U.S. Pat. No. 5,092,871 by Aebischer et al.) for repairing severed nerve ends have been described that place nerve ends in proximity to each other within a conduit of a guidance channel for promotion of nerve repair. This method is invasive and limited by the confines of the guidance channel.

Optical gradients have been used to interact with proteins, which are soft dielectrics. Optical tweezers (U.S. Pat. No. 5,079,169 by Chu et al and U.S. Pat. No. 5,245,466 by Burns et al) have been used to move and restrain biological particles, while optical stretchers (U.S. Pat. No. 6,067,859 by Kas & Guck) have been used to stretch and deform these dielectric materials. Current tools exploit optical gradients from a beam of light to manipulate the position of a small dielectric particle immersed in a fluid medium whose refractive index is smaller than that of the particle. These optical techniques have been generalized to enable manipulation of reflecting, absorbing, and low dielectric constant particles as well. Current optical trapping systems can manipulate single or multiple dielectric particle systems with one or more beam optical traps. Such systems have not been used to influence the growth or guide a cell.

SUMMARY OF THE INVENTION

This invention, in one broad respect, is a cell guidance method comprising defining a cell guidance path, wherein the light source has a power in the range from 2 mW to 2 W and a beam size between approximately 300 nm and 50 microns, and wherein the light source guides the direction of growth of a cell that is attached to a substrate.

BRIEF DESCRIPTION OF THE FIGS.

DETAILED DESCRIPTION

Figure 1:
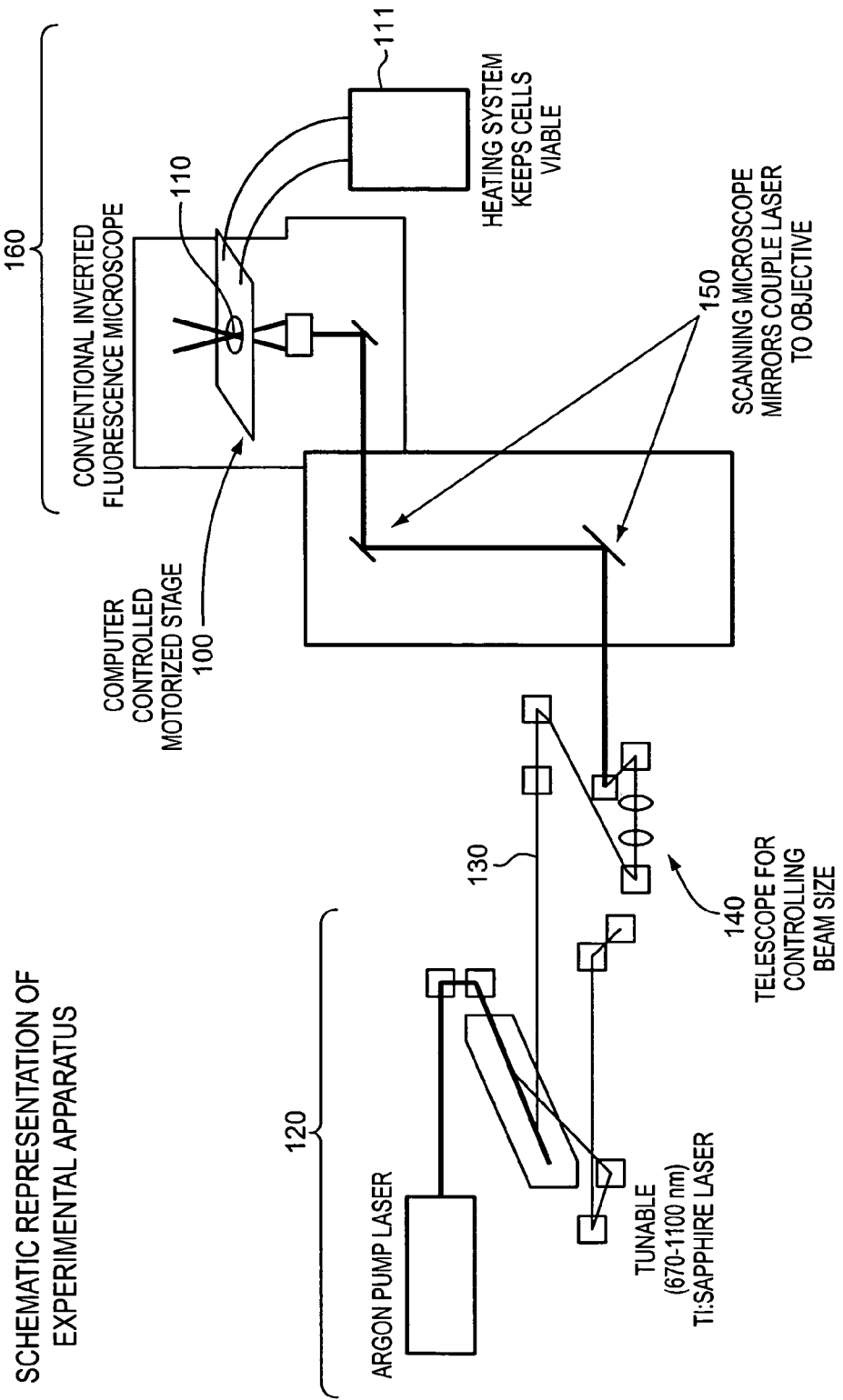
FIG. 1 illustrates an exemplary apparatus for Optical Cell Guidance.

Embodiments of the invention include Optical Cell Guidance (OCG), a novel method to control cell motility and/or growth. In certain embodiments, OCG guides the leading edge of motile cells with an optical gradient, which may bias a cell's motion into the light by pulling on proteins, which act like soft dielectrics in the electromagnetic field. OCG differs from those devices described above in that it controls the direction of cell motility or growth. This is an entirely new field, and the first device to directly manipulate cell growth. OCG differs from current approaches in that it does not trap or hold particles. Instead of trapping and pulling the cell, one of the goals of OCG is to influence the cells motility processes.

Generally, the method is capable of guiding many motile cell types, particularly neurons. There are many potential applications for such a guidance system. One such application is for in vitro circuits of real neurons. Neural circuits have received large popular attention in the multidisciplinary pursuit of unraveling mental processes. The implications reach from psychology to artificial intelligence models and biocomputing. Another important application is peripheral nerve repair. A system with the accuracy provided by OCG could redirect individual neurons to their distal stump quickly enough to maintain the connection's viability. A third application which has waited for a solution indefinitely is spinal trauma. Despite significant advances in the understanding of neurophysiology and spinal cord injury, a patient who suffers a complete spinal cord injury has little hope of recovery. Previous research has not yet yielded a way to stimulate the neuronal axons to regenerate the injured axonal structures and re-unite them with the motor neuron. Prior methods have also failed to replace the sensory axonal structures and unite them with their corresponding target cells. In other words, there has been some success in stimulating nerves to sprout, but not in accurately directing that modest growth or cell motility in a specifically desired direction. A method for producing or repairing the contact between cells may include guiding at least a portion of a first cell with a light beam; positioning the portion of a first cell such that it is near a second cell; and allowing at least one contact to be formed between the first cell and the second cell.

OCG is a new optical method for controlling the cell motility/growth direction and/or growth rate of cells, particularly neurons. Optical gradients and scattering forces interact with a dielectric placed in a light. As light passes through polarizable material, it induces a dipole moment. This dipole interacts with the electromagnetic field, one of whose resulting forces is directed towards the brighter region of the light, typically the focus of the beam. One can use brighter regions or focal points of light to pull or immobilize a dielectric target toward the focal region of light.

In one embodiment of the invention OCG may use a three dimensional laser path to bias the direction of cell motility and/or growth cones in neurons. Dielectric biological materials found in growth cones, including but not limited to the cell membrane and actin monomers involved in the cone's motility, are directed to the highest field potential. The gradient attempts to concentrate these materials in the center of the beam image, biasing polymerization and increasing the cone's motility in that area. In this way one optically guides a growth cone, manipulating motility to draw an arbitrary pattern on a substrate and connect by synapses to form neural networks.

OCG Apparatus

An exemplary optical cell guidance apparatus is illustrated in FIG. 1. Shown in FIG. 1 is a stage 100. The stage 100 may be used to position a target cell or a target cell population relative to the focus of a light beam 110. The stage 100 may be operatively coupled to a computer controlled motor or similar device to position the target appropriately, and subsequently scan through the desired path. The stage 100 may also be operatively coupled to a heating device 111 to maintain the proper conditions for cell motility and/or growth and maintenance.

Also shown in FIG. 1 is an exemplary light source 120, for example, comprising a green laser pumping a tunable Ti:sapphire laser. A light beam 130 produced by the light source 120 is directed into a telescope device 140 for controlling the size of the light beam 130. A light beam is then directed to a series of scanning microscope mirrors 150. Scanning microscope mirrors 150 direct a light beam into a conventional inverted fluorescence microscope 160 where it is focused in the approximate plane of a target that is positioned on the stage 100.

Light Source

In certain embodiments of the invention a light source is used to create an electric field for induction of dielectric properties within or on a cell membrane. The light intensity may induce a biological response without disrupting, moving, or damaging a cell. Light sources include but are not limited to Ti:sapphire laser, and other laser sources, such as diode lasers, NdYag, and others. Light sources include, but are not limited to, laser based, incandescent, emission lamps, arc lamps, and fluorescent sources. Light sources may be used at intensities in the approximate range of 2 mW to 2 W, where in certain embodiments a choice of approximately 20 to 100 mW is preferred. In certain embodiments the wavelength of a light source may be in the approximate range of 600 nm to approximately 1100 nm. In certain embodiments a light source with a wavelength in the approximate range of 750 nm to 850 nm is preferred. The wavelength and power of a light source may vary depending on the specific application. In one embodiment, the light source may be moved relative to a support, such as the stage 100 in FIG. 1, along a desired cell motility and/or growth path to define the cell guidance path. In other embodiments a series of static light patterns may be positioned to form a two-dimensional or three-dimensional path for cell guidance. In another embodiment the light source may be stationary and the support moved relative to the light source to define a cell guidance path.

Optics

Optical arrangements provide a variable effective beam size of the light source between approximately 300 nm and 50 microns, which allows for a broader distribution of gradient forces, or a smaller more focused illumination. This variable beam size, as well as variable power permits a diverse spectrum of interaction regimes. This selection allows the system to illuminate the growth cone and bias its direction, while allowing the cell to move under its own motility and prevent trauma to the cell.

The illumination area in certain embodiments covers a portion of the lamellipodia to bias the direction of lamellipodia motility and/or growth. The desire is not to pull the lamellipodia, but bias the direction of its own growth, guide the cell. The focus and the power of a light beam may be optimized for the control of lamellipodia motility/growth. In certain embodiments the optics may be designed for use with fiber optics for in vivo applications. In yet another alternative, the optics may be incorporated into a device that is implanted in an organism to provide a cell guidance path for extended periods of time.

Cell Types

Virtually any cell type that is capable of forming lamellipodia may be subjected to the methods and apparatus of the invention. Cells may include cells in vitro, in vivo, and/or in situ as well as cells that are implanted into an organism or located in a device, that may in turn be implanted in an organism. Cells that may be used in the methods of the invention include, but are not limited to neurons. In one embodiment, rat pheochromocytoma cells (PC-12 cells) that have been genetically modified to over-express the actin severing protein Gelsolin may be used. Alternatively, control PC-12 and rat neuroblastoma (NG108-15) may be used. Alternative cell types include, but are not limited to, fibroblasts, osteoclast, stem cells, leukocytes, keratocyte, metastatic cells, and other cell types.

Growth Media

Standard growth conditions are typically known for a variety of cell types and are used to support growth and maintenance of the cells. This information may be found in general cell culture protocols such as Spector, D. L. and Goldman, R. D. (Eds.) (1998), *Culture and Biochemical Analysis of Cells*, Cold Spring Harbor Laboratory Press. In the event that other novel cell types are used, one skill in the art would be capable of determining the growth conditions. For example, PC-12 rat pheochromocytoma and clones are cultured at 37° C. in RPMI 1640 medium with 10% horse serum and 5% fetal bovine serum (FBS), where neurites are induced reversibly with prime medium, which is identical to the recipe above with an added concentration of approximately 100 ng per micro liter of neuronal growth factor (NGF). NG 108-15 neuroblastoma cells are cultured in DMEM with 10% FBS.

Cell Substrates

In certain embodiments the cells may be guided over, through or on a two dimensional substrate. In other embodiments cell motility and/or growth may be guided within or on a three dimensional substrate. A substrate may be any material that provides for cell motility and/or growth and will preferably provide for cell attachment. Substrates include, but are not limited to plastics, glass, proteinaceous matrices, synthetic matrices, and the like. In particular, a substrate may be a coated plastic, coated glass with coatings including but not limited to laminin and poly-lysine. In certain embodiments, the cell motility and/or growth pattern may be a three-dimensional motility/growth pattern, in which case a three-dimensional substrate may be desired, such as a collagen matrix or gel.

The method of guiding cells, in particular neuronal growth cones, with optical gradients is new, and has many advantages over conventional methods, as described herein. Therefore, the invention is exceptionally accurate and can target a particular section of a growth cone with micron level precision. The OCG system is also dynamic, whereas conventional polymer techniques are static and require that each neuron's path be designed and printed before the cells are plated onto the substrate. OCG directs the nerves after they are plated, and can easily change patterns based on user input. This provides a highly dynamic rendering of arbitrary network patterns in a substrate without preparing a "wiring pattern" in the cell medium or substrate. OCG is also effective in three dimensions, moving easily between different points in the horizontal plane with mirrors or a movable stage. By focusing in different planes within a substrate, OCG can guide a growth cone through the z-axis, creating three-dimensional paths and patterns. OCG'S three-dimensional capabilities make it a natural choice for in vivo applications. OCG is far less invasive than other methods. By interacting with the neuron only using light, OCG can avoid contaminating the neurons or damaging them or surrounding tissue, with very precise control of the applied force. Built with "off the shelf" equipment: OCG can be implemented entirely with commercially available equipment, cutting out the monetary and time expense of custom components.

Normal short scale retractions, such as those associated with neuron growth, may be avoided by using chemical factors in combination with the optical guidance system described herein. Laser damage of a cell may be avoided by selecting optical wavelengths that are the least absorbed and/or by intermittently illuminating the target area. In one embodiment, cells have been nondestructively irradiated with power in excess of 1 Watt.

The invention may be used to create in vitro neuron systems, as well as guiding nerves in vivo to form new connections or reattaching nerves in trauma cases. In other embodiments the guidance systems described may be used to direct neurons onto a biological/semiconductor interface. Applications may range from synthetic prosthesis sensory control, treatments for paralysis, biocomputing, replacing nerve guidance channels, reversing some cases of blindness by reattaching retinas, and more.

OCG contributes a large set of potential directions to the study the motility of growth cones and neural networks. OCG can connect neurons via synapses, wiring different axons and cells together to create new network nodes in a highly controlled fashion.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 2:
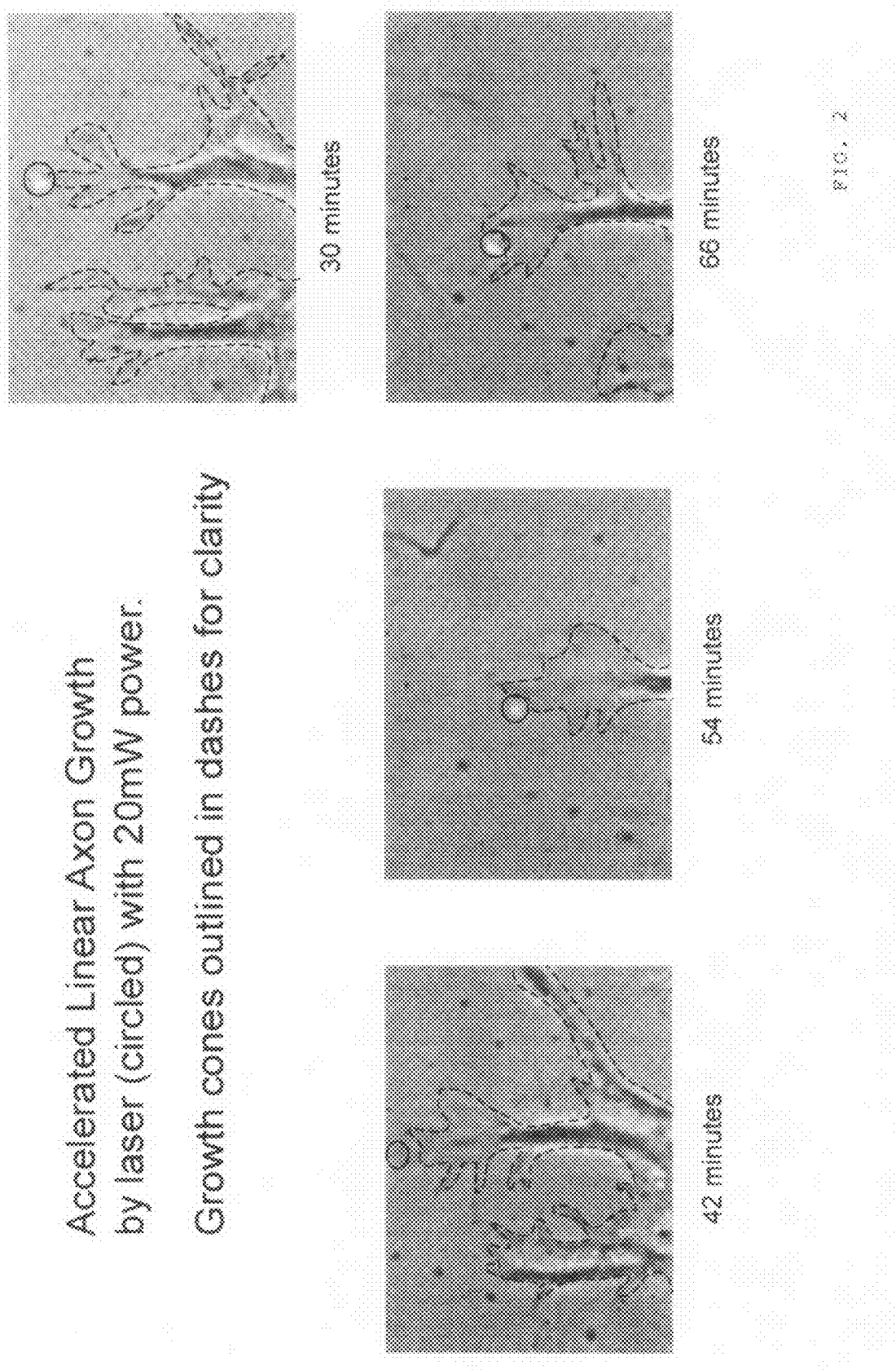
FIG. 2 illustrates an example of the guidance of a neuron.

FIG. 2 illustrates an example of neuronal guidance. A series of photographs in 12-minute increments are shown demonstrating the guidance of a neuron using the methods and techniques of the invention. The visible portions of the cell body are outlined with a dotted line and a circle designates the position of the light beam. Time zero shows a cell not yet under the influence of the light beam. During the time course the cell is guided to left in the photographs. This demonstrates the ability to guide a cell in a desired direction.

Example 2

Figure 3:
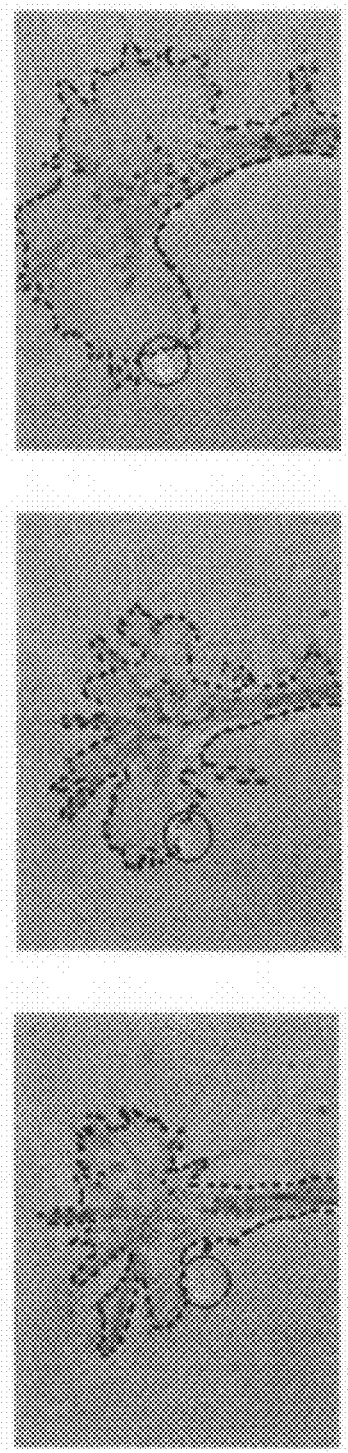
FIG. 3 illustrates an example of enhanced growth of neuron.
Figure 3:
Figure 3:
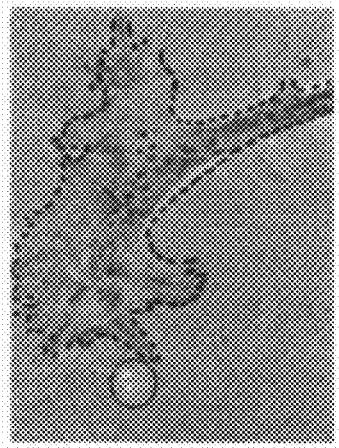

FIG. 3 illustrates an example of enhanced motility of an illuminated growth cone placed side by side with a control cell. A series of photographs in 12-minute increments are shown demonstrating the enhanced motility of a neuron using the methods and techniques of the invention. The visible portions of the cell body are outlined with a dotted line and a circle designates the position of the light beam. The 30 minute time point shows a neuronal growth cone under the influence of the light beam. During the time course the linear growth of the growth cone influenced by the light beam is enhanced, as compared to that of the growth cone not under the influence of the light beam. This demonstrates the ability to control the motility/growth of a neuron in a desired direction. A method for controlling cell motility/growth may include illuminating a portion of a cell; defining a motility/growth path for the portion of the cell, typically a growth cone; and controlling motility/growth of a growth cone in a desired direction.

What is claimed is:

1. A method of guiding the direction of growth of a neuron or neuronal precursor cell, comprising irradiating a portion of an edge of said neuron or said neuronal precursor cell attached to a substrate with light to guide the direction of growth of said cell, wherein the light is produced by a light source that has a power in the range from 2 mW to 2 W and a beam size between approximately 300 nm and 50 microns.

2. The method of claim 1, wherein the light source is a laser.

3. The method of claim 1, wherein cell guidance is performed in vivo.

4. The method of claim 1, wherein cell guidance is performed in vitro.

5. The method of claim 1, wherein cell guidance is performed in situ.

6. The method of claim 1, wherein the cell is an eukaryotic cell.

7. The method of claim 1, wherein the eukaryotic cell is a mammalian cell.

8. The method of claim 1, wherein the light source is directed through a telescope device.

9. The method of claim 1, wherein the light source is directed through an inverted fluorescence microscope.

10. The method of claim 1, wherein the light source has a wavelength in the range of about 750 nm to about 850 nm, with a power in the range of 20 to 100 mW.

* * * * *